US00PP37676P2

(12) United States Plant Patent
Garner

(10) Patent No.: US PP37,676 P2
(45) Date of Patent: Sep. 8, 2026

(54) IPOMOEA PLANT NAMED 'ISGFB11-0'

(50) Latin Name: *Ipomoea batatas*
Varietal Denomination: ISGFB11-0

(71) Applicant: Kenneth Nelson Garner, Trent Woods, NC (US)

(72) Inventor: Kenneth Nelson Garner, Trent Woods, NC (US)

( * ) Notice: Subject to any disclaimer, the term of this patent is extended or adjusted under 35 U.S.C. 154(b) by 0 days.

(21) Appl. No.: 19/549,987

(22) Filed: Feb. 25, 2026

Related U.S. Application Data

(60) Provisional application No. 63/768,963, filed on Mar. 8, 2025.

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1, 226, 258
CPC ..... A01H 5/02
See application file for complete search history.

*Primary Examiner* — Kent L Bell

(57) ABSTRACT

A new and distinct cultivar of *Ipomoea* plant named 'ISGFB11-0' is disclosed, characterized by burgundy foliage with a red tinge which resists fading in high light environments. Plants are dense and compact due to very short internodes. Foliage is distinctly finely pinnatisect. The new cultivar is an *Ipomoea* typically produced as an outdoor ornamental plant.

1 Drawing Sheet

Latin name of the genus and species: *Ipomoea batatas*.
Variety denomination: 'ISGFB11-0'.

BACKGROUND OF THE INVENTION

The new variety originated as a chance discovery by the inventor. The variety was discovered as a naturally occurring whole plant mutation from an unnamed, unpatented proprietary variety of *Ipomoea batatas*. The new variety was discovered in March 2023 at a research nursery in Trent Woods, North Carolina.

After selecting and isolating the new cultivar, asexual reproduction of the new cultivar 'ISGFB11-0' was first performed by vegetative tip cuttings in a commercial greenhouse in Somis, California in August 2023. 'ISGFB11-0' has since produced several generations and has shown that the unique features of this cultivar are stable and reproduced true to type. Typical asexual reproduction of the new variety is by vegetative cuttings.

SUMMARY OF THE INVENTION

The cultivar 'ISGFB11-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGFB11-0'. These characteristics in combination distinguish 'ISGFB11-0' as a new and distinct *Ipomoea* cultivar:

1. Dense, compact plants due to very short internodes.
2. Burgundy foliage color with a tinge of red.
3. Foliage resists fading in high light environments.

4. Finely pinnatisect foliage.
5. Glossy foliage

PARENTAL COMPARISON

Plants of the new cultivar 'ISGFB11-0' are similar to the parent in most horticultural characteristics. However, 'ISGFB11-0' differs in the following:

1. The new variety has fine, highly dissected foliage; the parent variety has broadly lobed foliage.
2. Foliage color of the new variety is burgundy with a tinge of red; foliage of the parent variety is black.
3. Plants of the new variety are more compact and denser than plants of the parent variety due to the shorter internodes.

COMMERCIAL COMPARISON

Plants of the new cultivar 'ISGFB11-0' can be compared to the commercial variety *Ipomoea batatas* 'ISGHP05-2' U.S. Plant Pat. No. 32,057. Plants of 'ISGFB11-0' are similar to plants of 'ISGHP05-2' in most horticultural characteristics, however, plants of 'ISGFB11-0' differ in the following:

1. The new variety has fine pinnatisect foliage; this comparator has cordate foliage.
2. Foliage color of the new variety is burgundy with a tinge of red; foliage of this comparator is greyed-purple without a red tinge.
3. Plants of the new variety are more compact and denser than plants of this comparator due to shorter internodes.

Plants of the new cultivar 'ISGFB11-0' can be compared to the commercial variety *Ipomoea batatas* 'ISGDP01-1', U.S. Plant Pat. No. 31,725. Plants of 'ISGFB11-0' are similar to plants of 'ISGDP01-1' in most horticultural characteristics, however, plants of 'ISGFB11-0' differ in the following:

1. The new variety has fine pinnatisect foliage; this comparator has foliage with 2 deep and 2 moderately deep lobes.
2. Foliage color of the new variety is burgundy with a tinge of red; foliage of this comparator is greyed-purple without a red tinge.
3. Plants of the new variety are more compact and denser than plants of this comparator due to shorter internodes.

BRIEF DESCRIPTION OF THE PHOTOGRAPH

The accompanying photograph illustrates in full color a typical plant of 'ISGFB11-0' grown in a greenhouse in Somis, California. This plant is approximately 24 weeks old, shown in a 12-inch pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to the R.H.S. Colour Chart, 2007, except where general terms of ordinary dictionary significance are used. The following observations and measurements describe 'ISGFB11-0' plants grown during the Spring months in a greenhouse in Somis, California, under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGFB11-0'.

Age of the plant described: Approximately 8 weeks from an unrooted cutting.

Container size of the plant described: 12 inches.

Propagation:
- *Propagation method.*—Terminal cuttings.
- *Time to develop roots suitable for transplanting.*—Summer: About 6 days at an average temperature of 24° C. Winter: About 10 days at an average temperature of 24° C.
- *Root description.*—Thick, fleshy. Roots colored closest to R.H.S. Yellow-White 158A.
- *Tuber description.*—Not observed to date.

Plant:
- *Growth habit.*—Compact.
- *Height.*—Approximately 17 cm from top of soil line.
- *Plant spread.*—Approximately 35 cm.
- *Growth rate.*—Rapid.
- *Branching characteristics.*—Very free branching, alternate or whorled occurring.

Primary lateral branches:
- *Length.*—12 to 20 cm.
- *Diameter.*—4 mm.
- *Texture.*—Very short pubescence.
- *Color.*—R.H.S. Greyed-Purple 187B.
- *Strength.*—Strong, flexible.
- *Internode length.*—Average range 3 to 6 mm.
- *Adventitious roots at nodes.*—Not observed.

Secondary lateral branches:
- *Length.*—5 to 10 cm.
- *Diameter.*—3 to 4 mm.
- *Texture.*—Very short pubescence.
- *Color.*—R.H.S. Greyed-Purple 187B.
- *Strength.*—Strong, flexible.
- *Internode length.*—5 to 8 mm.
- *Quantity per plant.*—Approximately 15 per primary branch.
- *Adventitious roots at nodes.*—Not observed.

New shoot growth characteristics:
- *Color.*—R.H.S. Greyed-Purple 187B.
- *Aspect.*—Upright.
- *Texture.*—Glabrous.

Foliage:
- *Arrangement.*—Alternate.
- *Average length.*—8 cm.
- *Average width.*—8 cm.
- *Shape of blade.*—Pinnatisect, 3 sections.
- *Apex.*—Acute.
- *Base.*—Cordate.
- *Margin.*—Entire.
- *Aspect.*—Upward fold and petiole attachment.
- *Texture of top surface.*—Glabrous
- *Texture of bottom surface.*—Glabrous
- *Appearance of bottom surface.*—Glossy
- *Appearance of top surface.*—Matte
- *Quantity of leaves per lateral branch.*—Average 15.

Foliage color:
- *Young foliage upper side.*—R.H.S. Greyed-Red 182A with a tinge Red 53C.
- *Young foliage under side.*—R.H.S. Greyed-Red 182C.
- *Mature foliage upper side.*—R.H.S. Greyed-Purple 187A with a tinge Red 53A and 53B.
- *Mature foliage under side.*—R.H.S. Greyed-Purple 187B.

Venation
- *Type.*—Palmate, reticulate.
- *Venation color, upper side.*—R.H.S. Greyed-Purple 187B.
- *Venation color, under side.*—R.H.S. Greyed-Purple 187B.

Petiole:
- *Length.*—2 to 5 cm.
- *Diameter.*—3 mm at base, 2 mm at top.
- *Texture.*—Very slightly hirsute.
- *Color.*—R.H.S. Greyed-Purple 187B.
- *Strength.*—Strong, flexible.
- *Aspect.*—Straight to slightly curved.

Flower:
- *Flowering not observed to date.*

Other characteristics:
- *Seeds and fruits.*—No seeds/fruits observed.
- *Disease/pest resistance.*—Neither resistance nor susceptibility to the normal pests and diseases of *Ipomoea* has been observed.
- *Temperature tolerance.*—Tolerates low temperatures to approximately 2° C. Good high-temperature tolerance observed to at least 40° C.

What is claimed is:

1. A new and distinct cultivar of *Ipomoea* plant named 'ISGFB11-0' as herein illustrated and described.

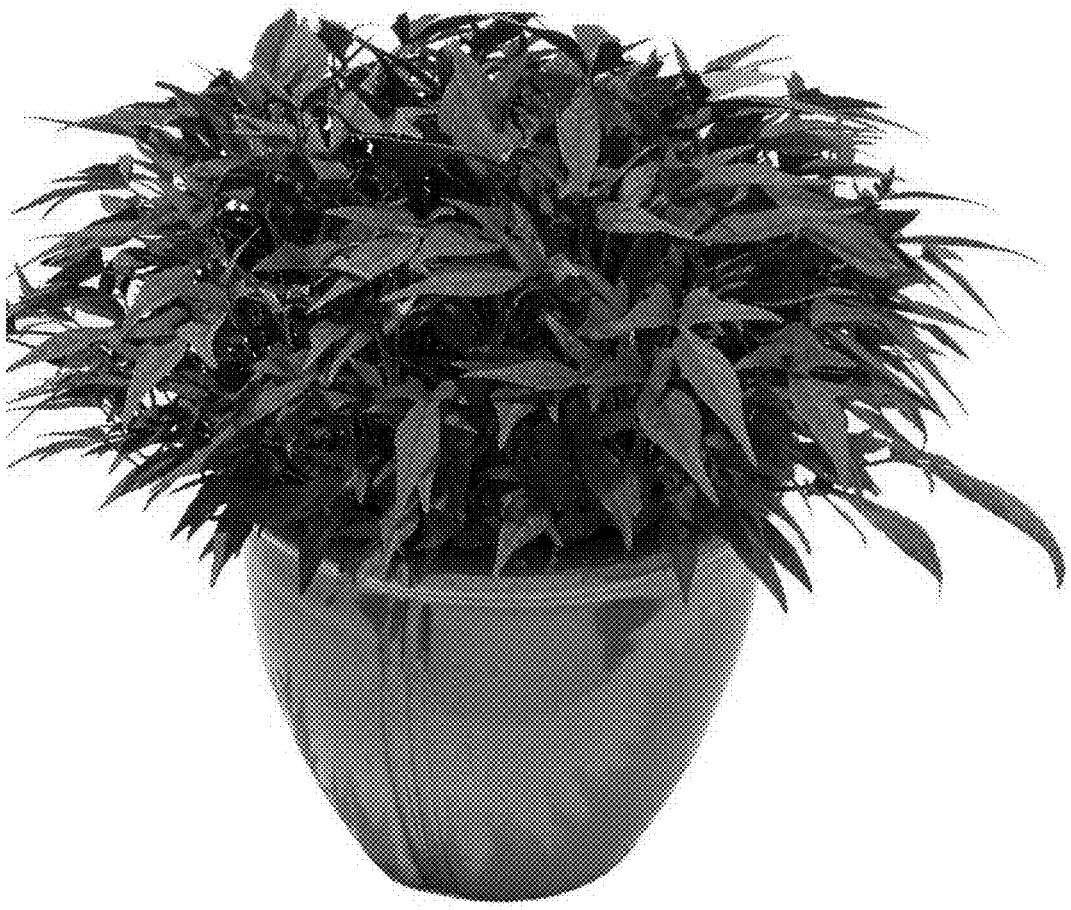

* * * * *